United States Patent
Wulfcrona et al.

(10) Patent No.: US 10,610,697 B2
(45) Date of Patent: Apr. 7, 2020

(54) MAGNOTHERAPY STRAP

(71) Applicant: Restpad Scandinavia AB, Skänninge (SE)

(72) Inventors: Johan Wulfcrona, Skänninge (SE); Oskar Svensson, Skänninge (SE)

(73) Assignee: Restpad Scandinavia AB (SE)

( * ) Notice: Subject to any disclaimer, the term of this patent is extended or adjusted under 35 U.S.C. 154(b) by 693 days.

(21) Appl. No.: 14/768,991

(22) PCT Filed: Feb. 19, 2014

(86) PCT No.: PCT/SE2014/050204
§ 371 (c)(1),
(2) Date: Aug. 19, 2015

(87) PCT Pub. No.: WO2014/129959
PCT Pub. Date: Aug. 28, 2014

(65) Prior Publication Data
US 2016/0001093 A1 Jan. 7, 2016

(30) Foreign Application Priority Data
Feb. 20, 2013 (SE) .................................. 1350205-9

(51) Int. Cl.
*A61N 2/06* (2006.01)
*A61N 2/00* (2006.01)
*G01L 5/04* (2006.01)

(52) U.S. Cl.
CPC ............... *A61N 2/06* (2013.01); *A61N 2/004* (2013.01); *G01L 5/04* (2013.01)

(58) Field of Classification Search
CPC ........ A61N 2/004; A61N 2/006; A61N 2/008; A61N 2/02; A61N 2/06; A61N 2/00; G01L 5/04
(Continued)

(56) References Cited

U.S. PATENT DOCUMENTS 4,730,646 A   3/1988  Traub
5,642,739 A * 7/1997  Fareed .................. A61F 5/0118
                                                128/878

(Continued)

FOREIGN PATENT DOCUMENTS

EP   1665947 A1   6/2006
EP   1803425 A1   7/2007

(Continued)

OTHER PUBLICATIONS

International Search Report for Application No. PCT/SE/2014/050204 dated Jun. 25, 2014.

*Primary Examiner* — Carrie R Dorna
(74) *Attorney, Agent, or Firm* — Lerner, David, Littenberg, Krumholz & Mentlik, LLP

(57) ABSTRACT

A magnotherapy strap (1) is provided comprising a carrier (3), one or more magnets (5) provided in the carrier (3). A band (7) is attached to the carrier (3) and is arranged to hold the carrier (3) against a limb (9) of a user. The strap further comprises an eye (11) provided at a first end (13) of the strap (1) through which a free end (15) of the band (7) is threadable, so as to allow tensioning of the strap (1) around the limb (9) of the user. The band (7) is provided with a pattern (17) indicating a length of the band (7) being threaded through the eye (11) to thereby indicate a degree of tension being applied to the limb (9).

20 Claims, 2 Drawing Sheets

(58) Field of Classification Search
USPC .......................................... 600/9, 10, 13–15
See application file for complete search history.

(56) References Cited

U.S. PATENT DOCUMENTS

| | | |
|---|---|---|
| 5,782,743 A | 7/1998 | Russell |
| 6,129,659 A | 10/2000 | Wilk |
| 6,152,893 A * | 11/2000 | Pigg ..................... A61F 5/0111 |
| | | 602/60 |
| 6,623,419 B1 | 9/2003 | Smith et al. |
| 7,617,615 B1 | 11/2009 | Martorell et al. |
| 2003/0045826 A1 | 3/2003 | Meyer |
| 2009/0168612 A1 | 7/2009 | Robin et al. |

FOREIGN PATENT DOCUMENTS

| | | |
|---|---|---|
| GB | 2367008 A | 3/2002 |
| WO | 9306887 A1 | 4/1993 |

* cited by examiner

MAGNOTHERAPY STRAP

CROSS-REFERENCE TO RELATED APPLICATIONS

The present application is a national phase entry under 35 U.S.C. § 371 of International Application No. PCT/SE2014/050204 filed Feb. 19, 2014, published in English, which claims the benefit of the filing date of Swedish Patent Application No. 1350205-9 filed Feb. 20, 2013, all of which are incorporated herein by reference.

TECHNICAL FIELD

The present invention relates to a magnotherapy strap.

BACKGROUND

Magnotherapy straps are known in the art and are used to help relieving symptoms of certain ailments and/or illnesses in humans and animals without the use of drugs. Generally, magnotherapy straps are believed to have an effect due to a combination of applied tension/pressure of the strap and magnetic fields of the magnets. It is common that magnotherapy straps are worn by a user over a prolonged period of time, such as when worn during sleep or during a flight. Some of the magnotherapy straps known in the art comprise fastening/tensioning means in the form of a band via which a user may tension the strap circumferentially around a limb. Two such magnotherapy straps are described in the documents U.S. Pat. No. 5,642,739 A and GB 2367008 A. When tensioning such a strap, a user might tension the strap to a degree of tension exceeding a safe degree of tension with regard to blood flow and/or alleged effect. Also, when worn over a prolonged period of time a high degree of tension of the strap will cause discomfort, and may be potentially dangerous due to a reduced blood flow. Therefore, there is a need for a magnotherapy strap which can reduce the risk of incorrect use.

SUMMARY

An object of the present invention is to provide a magnetic strap reducing the risk of incorrect use.

According to an aspect of the invention, the object is achieved by a magnotherapy strap comprising a carrier, one or more magnets provided in the carrier, a band being attached to the carrier and arranged to hold the carrier against a limb of a user, and an eye provided at a first end of the strap through which a free end of the band is threadable, so as to allow tensioning of the strap around the limb of the user, wherein the band is provided with a pattern indicating a length of the band being threaded through the eye to thereby indicate a degree of tension being applied to the limb, wherein the band is stretchable so as to allow stretching of the band along a direction of extension of the band.

Since the degree of tension being applied to the limb is indicated, a magnotherapy strap is provided reducing the risk of incorrect use.

As a result, the above mentioned object is achieved.

Also, a safer strap than those described in the prior-art is provided since the user can recognize the tension being applied to the limb, via the pattern indicating a length of the band being threaded through the eye.

Further, since the tension being applied to the limb is visibly indicated via the arrangement, a user having reduced sensitivity in a limb may apply a suitable tension to the limb without sensing the tension.

Since the band is stretchable, the degree of tension being applied to the limb may be indicated, via the length of which the band is threaded through the eye, with improved accuracy. Accordingly, the stretchability of the band may be co-designed with the pattern such that the stretchability together with a length of features of the pattern corresponding to a length of the band being threaded through the eye results in a predetermined tension of the strap. Thereby, the risk of incorrect use is further reduced. Also, since the band is stretchable, the strap is comfortable to use.

According to some embodiments, the pattern comprises lines, numbers, and/or colours having shifting appearance along a length of the pattern. In such embodiments, due to the pattern comprising lines, numbers, and/or colours having shifting appearance along a length of the pattern, a user may easily recognise the length of the band being threaded through the eye, and thus also recognize a degree of tension being applied to the limb. Thereby, the risk of incorrect use is further reduced.

According to some embodiments, the carrier comprises an inner surface being arranged to abut against the limb of the user, wherein the pattern is provided on a first surface of the band, and wherein the first surface faces in the same direction as the inner surface in an un-threaded state of the strap, the pattern being provided on the first surface such that an increasing amount of the pattern becomes visible to the user when the strap is tensioned in a threaded state of the strap. Since an increasing amount of the pattern becomes visible to the user, a user may perceive the length of the band being threaded through the eye in an easy manner and thus also may perceive the degree of tension being applied to the limb in an easy manner. Thereby, the risk of incorrect use is further reduced.

According to some embodiments, the strap comprises a first and a second fastening means provided on a second surface of the band, being opposite to the first surface, wherein the first fastening means is provided in a region of the free end of the band, and wherein the first fastening means is arranged to mate with the second fastening means when the band is folded in a threaded state of the strap to thereby fasten the band. Since the first fastening means is arranged to mate with the second fastening means, the band is easy to fasten. Since the band is easy to fasten, the strap is easy to use and easy to fasten around the limb of the user.

According to some embodiments, the one or more magnets are supple. Since the one or more magnets are supple, the one or more magnets will assume a form suitable for the limb of a user when tensioning of the strap, and the strap will be comfortable to use.

According to some embodiments, the strap comprises at least three elongated magnets being provided in the carrier such that a direction of extension of the elongated magnets coincides with a direction of extension of the strap. Since the strap comprises at least three elongated magnets being provided in the carrier such that a direction of extension of the elongated magnets coincides with a direction of extension of the strap, the magnets will cover a large area of the carrier and thus also cover a large area of the limb of the user.

According to some embodiments, the at least three elongated magnets are provided in the carrier with a mutually alternating polarity. Since the at least three elongated magnets are provided in the carrier with a mutually alternating polarity, a contractile magnetic force between the magnets are obtained.

According to some embodiments, the eye is provided at a first end of the band, being opposite to the free end, or at one end of the carrier. Since the eye is provided at a first end of the band, being opposite to the free end, or at one end of the carrier, the strap is easy to manufacture and easy to use.

According to some embodiments, the strap is arranged to be tensioned around a calf of a user to thereby relieve stress suffered from restless legs syndrome. Studies have shown that tension applied around a calf of a user in combination with the magnets provides an advantageous effect in relieving stress suffered from restless legs syndrome. Therefore, since the strap indicates tension being applied to the limb, a user may apply a desired tension to the limb and the effect may be improved.

Further features of, and advantages with, the present invention will become apparent when studying the appended claims and the following detailed description. Those skilled in the art will realize that different features of the present invention may be combined to create embodiments other than those described in the following, without departing from the scope of the present invention, as defined by the appended claims.

BRIEF DESCRIPTION OF THE DRAWINGS

The various aspects of the invention, including its particular features and advantages, will be readily understood from the following detailed description and the accompanying drawings, in which.

DETAILED DESCRIPTION

The present invention will now be described more fully with reference to the accompanying drawings, in which example embodiments are shown. However, this invention should not be construed as limited to the embodiments set forth herein. Disclosed features of example embodiments may be combined as readily understood by one of ordinary skill in the art to which this invention belongs. Like numbers refer to like elements throughout.

Well-known functions or constructions will not necessarily be described in detail for brevity and/or clarity.

Figure 1:
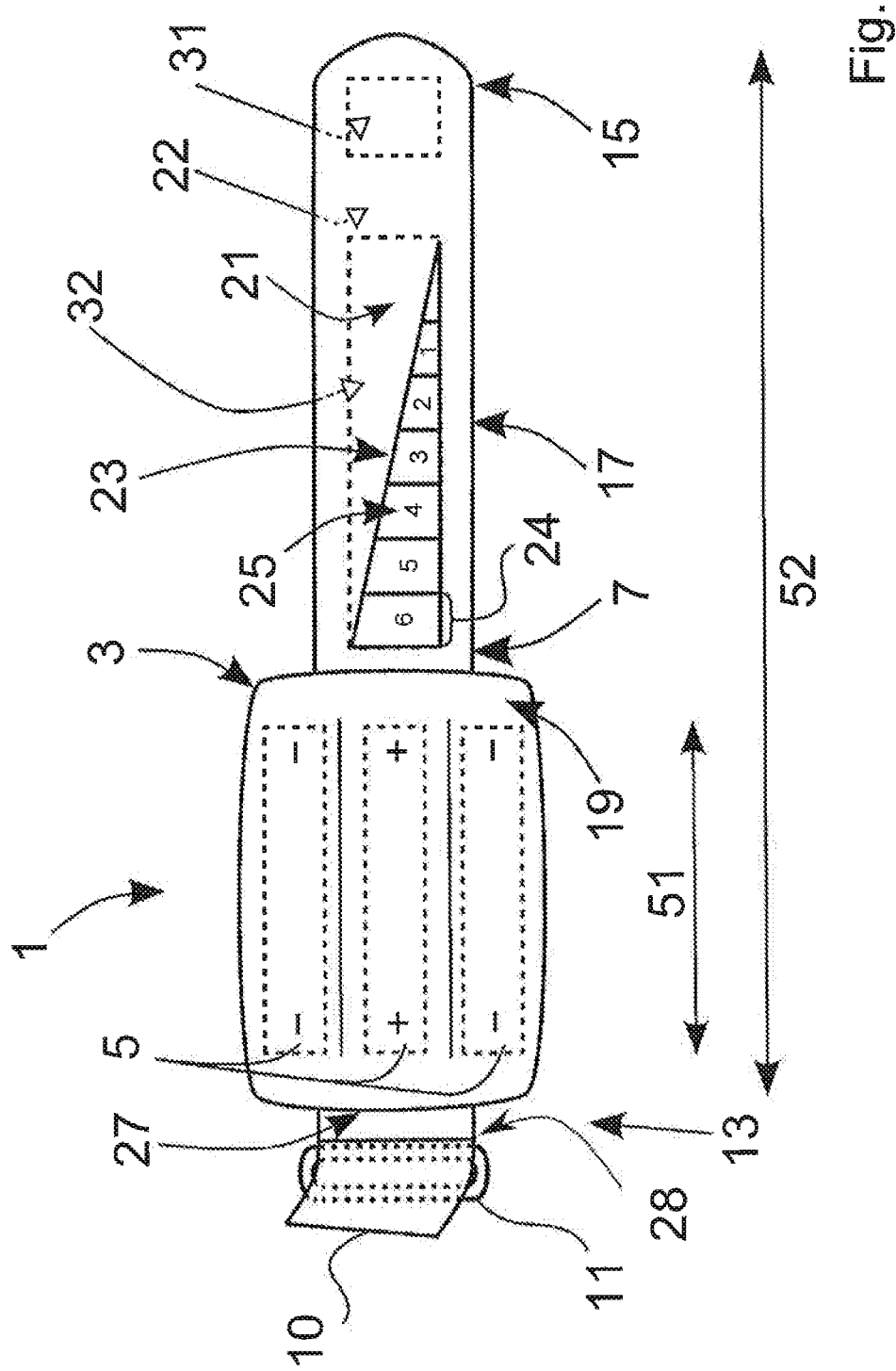
FIG. 1 illustrates a magnotherapy strap in an un-threaded state according to some embodiments.

FIG. 1 illustrates a magnotherapy strap 1 in an un-threaded state according to some embodiments. The strap 1 comprises a carrier 3 in which three elongated magnets 5 are provided. A band 7 is attached to the carrier 3 and arranged to hold the carrier 3 against a limb of a user. An eye 11 is provided at a first end 13 of the strap 1 through which a free end 15 of the band 7 is threadable, so as to allow tensioning of the strap 1 around the limb of the user. The band 7 is provided with a pattern 17 indicating a length of the band 7 being threaded through the eye 11 to thereby indicate a degree of tension being applied to the limb.

The pattern 17 comprises lines 23 and numbers 25 having a shifting appearance along a length of the pattern 17 and thus also along a length of the band 7. Such lines may be lines provided in a perpendicular direction in relation to the length of the band 7. Also, a first line may be provided in a direction extending essentially along the length of the band 7 and a second line may be provided at an angle to the length of the band 7 to thereby form segments having a shifting extension in a direction perpendicular to the length of the band 7. Also, such segments may be provided with different numbers along the length of the band 7. Due to these features, a user may easily recognise the length of the band 7 having been threaded through the eye 11 in a threaded state of the strap 1. In addition, in order to further facilitate recognition of the length of the band 7 having been threaded through the eye 11 in a threaded state of the strap 1, the segments, and/or any other features of the pattern 17, may be provided in colour/colours having a shifting colour scale along the length of the pattern 17. For example, in the pattern 17 illustrated in FIG. 1, the segment positioned to the right of the segment provided with the number "1", i.e. the rightmost segment illustrated in FIG. 1, may be provided in a clear yellow colour and the segment 24 provided with the number "6", i.e. the leftmost segment illustrated in FIG. 1, may be provided in a clear red colour, wherein the segments in-between these segments are provided in colours having a colour-scale shifting from yellow to red in a direction from the right to the left in FIG. 1. Thereby, a user can easily recognise the length of the band 7 having been threaded through the eye 11 in a threaded state of the strap 1, and thus also recognize a degree of tension being applied to the limb.

The pattern 17 may be provided with features other than those described above. For example, the pattern 17 may comprise lines provided in a direction perpendicular to the length of the band 7, and/or a single strip having a form of an elongated triangle, and/or the pattern 17 may only comprise numbers having a shifting value along the length of the pattern 17, and/or the pattern 17 may only comprise colour/colours having shifting colour scale along the length of the pattern 17. Also, the pattern 17 may comprise a combination of two or more of the features described above.

Further, the pattern 17 may comprise lines forming rectangular segments having a size shifting along the length of the pattern 17. Such rectangular segments may be provided such that an extension of the rectangular segments increases in a direction perpendicular to the length of the band 7. Also, as with the example with the segments described above, such rectangular segments each may be provided with different numbers and/or colours having shifting colour-scales along the length of the pattern 17.

The carrier 3 comprises an inner surface 19 being arranged to abut against the limb of the user. The inner surface 19 of the carrier 3 may be formed by a material admitting breathing and transportation of sweat. The inner surface 19 of the carrier 3 may be formed by a breathable, laminated material comprising poly amide, elastomer, and/or foam. The pattern 17 is provided on a first surface 21 of the band 7, which first surface 21 faces in the same direction as the inner surface 19 of the carrier 3 in the un-threaded state of the strap 1, as illustrated in FIG. 1.

The carrier 3 is provided with an outer layer formed by fabric material. The carrier 3 may further comprise foam material arranged to provide comfort to a user. The carrier 3 further comprises one or more pockets accommodating the one or more magnets 5. The strap 1 illustrated in FIG. 1 comprises three pockets accommodating three elongated magnets 5. As can be seen, the elongated magnets 5 are provided side by side with a direction of extension 51 coinciding with a direction of extension 52 of the strap 1. Thereby, the magnetic fields of the magnets 5 cover a substantive area of the limb of the user. Also, as indicated by the symbols "+" and "−" in FIG. 1, the magnets 5 are provided in the carrier 3 with a mutually alternating polarity. The magnet accommodated in the middle pocket is illustrated with the symbols "+" indicating that this magnet is positioned in the pocket such that a positive pole of the magnet faces in the same direction as the inner surface 19 of the carrier 3 in the un-threaded state of the strap 1. Thereby the positive pole of this magnet will face the limb of the user in the threaded state of the strap 1. Accordingly, the negative pole of the magnet accommodated in the pocket in the middle faces in a direction opposite to the inner surface 19 of the carrier 3 and thereby away from the limb of the user in the threaded state of the strap 1. Also, as illustrated in FIG. 1, the two magnets being accommodated in the two pockets being adjacent to the middle pocket are illustrated with the symbols "−" indicating that these magnets are positioned in the pockets such that a negative pole of these magnets faces in the same direction as the inner surface 19 of the carrier 3 in the un-threaded state of the strap 1. Thereby the negative pole of these magnets will face the limb of the user in the threaded state of the strap 1. Accordingly, the positive poles of these magnets face in a direction opposite to the inner surface 19 of the carrier 3 and thereby away from the limb of the user in the threaded state of the strap 1. The one or more magnets 5 comprised in the strap 1 may be supple so as to adapt at least partially to a curvature of a limb of a user. The one or more magnets 5 may be ferrite ceramic strontium magnets 5 with a field strength ranging from 2-5 mT (micro tessla).

The eye 11 may comprise a plastic material and comprises an opening suitable for receiving the band 7. The eye 11 may be provided at a first end 28 of the band 7, being opposite to the free end 15 of the band 7, as illustrated in FIG. 1, or at one end 27 of the carrier 3.

The strap 1 further comprises a tab 10 provided at a first end 28 of the band 7 being opposite to the free end 15 of the band 7. As an alternative, the tab 10 is provided at one end 27 of the carrier 3. The tab 10 is arranged to form a padding between the eye 11 and the limb of a user during use of the strap 1, i.e. in the threaded state of the strap 1. The tab 10 comprises a soft material to provide comfort to a user. In combination, the tab 10 may further comprise a stiff material to facilitate positioning of the tab between the eye 11 and the limb of a user when the strap is to be used.

Figure 2:
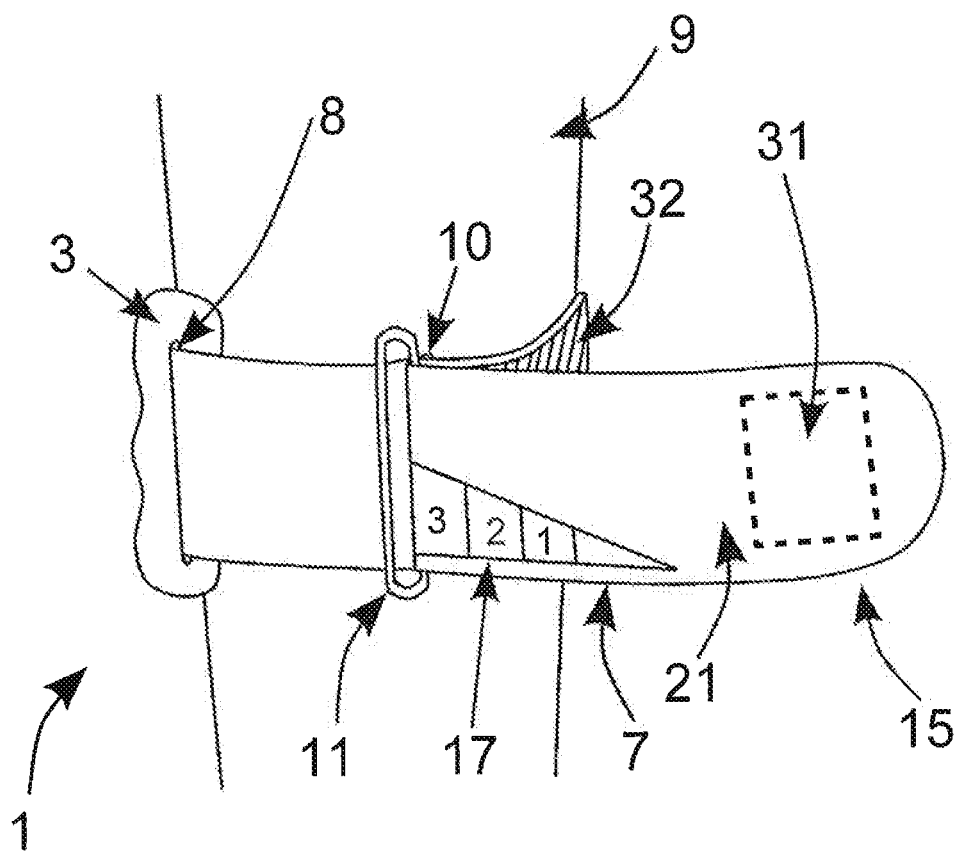
FIG. 2 illustrates the magnotherapy strap in a threaded state according to some embodiments.

FIG. 2 illustrates the magnotherapy strap 1 in a threaded state according to some embodiments. Here, the free end 15 of the band 7 has been threaded through the eye 11 and the strap 1 has been positioned around a calf 9 of a user.

As illustrated in FIG. 2, since the pattern 17 is provided on the first surface 21 of the band 7, as described with reference to FIG. 1, an increasing amount of the pattern 17 will become visible to the user when the strap 1 is tensioned in the threaded state of the strap 1. Thereby, a user may easily recognise the length of the band 7 being threaded through the eye 11 in the threaded state of the strap 1, and thus also recognize a degree of tension being applied to the calf 9.

The band 7 may be stretchable so as to allow stretching of the band 7 along the direction of extension of the band 7. The band 7 may comprise fabric and elastomeric material. The band 7 may be attached to the carrier 3 by extending through a duct 8 provided on the carrier 3, as illustrated in FIG. 2, wherein the band 7 extends through the duct 8 in the carrier 3. The band 7 may be slidably received in the duct 8, i.e. the band 7 may be slidably attached to the carrier 3. As an alternative, the band 7 may be attached to the carrier 3 by means of sewing.

Also, as illustrated in FIG. 2, in the threaded state of the strap 1, the tab 10 is positioned between the eye 11 and the limb 9 of a user to thereby form a padding between the eye 11 and the limb 9 of a user. Irritation resulting from a contact between the eye 11 and the limb 9 of a user can thereby be avoided.

A user may be instructed to position the strap 1 at a desired position around a limb 9 and then to thread the band 7 through the eye 11 and pull the free end 15 of the band 7 such that the band 7 abuts the limb 9 without any considerable tension. Then, the user is instructed to recognise an aspect of the pattern 17 being visible, such as the highest number of the pattern 17 being visible, e.g. number 3 as illustrated in FIG. 2. Then, the user is instructed to pull the free end 15 of the band 7 such that the features of the pattern 17 being visible changes in a particular way, for example that the highest number being visible increases by two steps, e.g. that the highest number visible, number 3 illustrated in FIG. 1 is increased to number 5. In this way, a user may achieve a tension being within a predetermined tension interval, despite the fact that users have differently sized limbs and may position the strap 1 at different positions on the limb.

Also, a user may be instructed to position the strap 1 at a desired position around a limb 9 and then to thread the band 7 through the eye 11 and pull the free end 15 of the band 7 such that the band 7 abuts the limb 9 without any considerable tension. Then, the user is instructed to recognise the highest number of the pattern 17 being visible, e.g. number 3 as illustrated in FIG. 2. Then, the user is instructed to pull the free end 15 of the band 7 such that the highest number being visible increases by one step. Then, the user may be instructed to further pull the free end 15 of the band 7 such that the highest number being visible increases by zero to one step further. In the example shown in FIG. 2, this corresponds to the user starting from the highest number being visible, i.e. number 3 and pulls the free end 15 such that the highest number being visible increases to number 4. Then the user is given the instruction to pull the free end 15 zero to one step further i.e. such that an area of the pattern becomes visible being somewhere in between the number 4 and the number 5. In this way, a user may achieve a tension being within a preferred tension interval, and at the same time is given the opportunity to apply a tension suitable for personal preferences.

Thus, the stretchability of the band 7 and a relative distance between features of the pattern 17, such as the numbers of the pattern 17, may be co-designed such that a tension being within a preferred tension interval is obtained by pulling on the free end 15 of the band 7 such that the features of the pattern 17 being visible changes in a particular way, for example that the highest number being visible is increases by two steps. Since a user is able to apply a tension being within a preferred tension interval with the strap, when following the instructions above, an improved magnotherapy strap is provided. Such preferred tension interval may for example be 12-32 N, or 17-27 N, or 20-24 N, or 21-23 N.

According to some embodiments, the strap 1 is arranged to be tensioned around a calf of a user to thereby relieve stress suffered from restless legs syndrome. Studies have shown that applied tension being in the interval 17-27 N in combination with magnets provides an advantageous effect in relieving stress suffered from restless legs syndrome. Therefore, in such embodiments, the strap is arranged such that, when following the instructions, a tension is obtained being in the interval of 17-27 N.

As illustrated in FIG. 1, the strap 1 comprises a first and a second fastening means 31, 32 provided on a second surface 22 of the band 7, being opposite to the first surface 21, wherein the first fastening means 31 is provided in a region of the free end 15 of the band 7. The first fastening means 31 is arranged to mate with the second fastening means 32 when the band 7 is folded on top of itself in the threaded state of the strap 1, as illustrated in FIG. 2, to thereby fasten the band 7 and thus also fasten the strap 1. Thereby, a user may easily fasten the band 7 and thus also the strap 1 around the limb 9 without obtaining a loose portion of the band 7. The first and second fastening means 31, 32 may comprise a hook and loop fastening system such as the Velcro (c) system, or buttons, or snap fasteners.

Therefore, it is to be understood that the foregoing is illustrative of various example embodiments and the invention is not to be limited to the specific embodiments disclosed and that modifications to the disclosed embodiments, combinations of features of disclosed embodiments as well as other embodiments are intended to be included within the scope of the appended claims.

The invention claimed is:

1. A magnotherapy strap comprising:
a carrier;
one or more magnets provided in the carrier;
a band being attached to the carrier and being arranged to hold the carrier against a limb of a user, the carrier having an inner surface comprising a breathable material; and
an eye provided at a first end of the strap through which a free end of the band is threadable, so as to allow tensioning of the strap around the limb of the user,
wherein the band is provided with a pattern indicating a length of the band being threaded through the eye to thereby indicate a single value of a plurality of predetermined degrees of tension being applied to the limb, and
wherein the band is elastic and stretchable so as to allow stretching of the band along a direction of extension of the band to achieve a desired degree of tension chosen from the plurality of predetermined degrees of tension indicated by the pattern.

2. The strap according to claim 1, wherein the pattern comprises one or more of lines, numbers and colours, the pattern having a shifting appearance along a length of the pattern.

3. The strap according to claim 1, wherein the inner surface of the carrier is arranged to abut against the limb of the user, and wherein the pattern is provided on a first surface of the band, and wherein the inner surface and the first surface face a first direction in an un-threaded state of the strap, the pattern being provided on the first surface such that an increasing amount of the pattern becomes visible to the user when the strap is tensioned in a threaded state of the strap.

4. The strap according to claim 3, wherein the strap comprises a first and a second fastening means provided on a second surface of the band, the second surface being opposite to the first surface, wherein the first fastening means is provided in a region of the free end of the band, and wherein the first fastening means is arranged to mate with the second fastening means when the band is folded in a threaded state of the strap to thereby fasten the band.

5. The strap according to claim 1, wherein the one or more magnets are supple.

6. The strap according to claim 1, wherein the strap comprises at least three elongated magnets being provided in the carrier such that a direction of extension of the elongated magnets coincides with a direction of extension of the strap.

7. The strap according to claim 6, wherein the at least three elongated magnets are provided in the carrier with a mutually alternating polarity.

8. The strap according to claim 1, wherein the eye is provided at a first end of the band, the first end being opposite to the free end, or at one end of the carrier.

9. The strap according to claim 1, wherein the strap is arranged to be tensioned around a calf of a user to thereby relieve stress suffered from restless legs syndrome.

10. The strap according to claim 1, wherein when the band is threaded through the eye, the desired degree of tension is a predetermined tension interval determined based on the pattern indicated between the eye at a first position on the pattern and the eye at a second position on the pattern.

11. The strap according to claim 10, wherein the band is not subject to tension in the first position.

12. A magnotherapy strap comprising:
a carrier including an inner surface being arranged to abut against a limb of a user, the inner surface comprising a breathable laminated material;
one or more magnets provided in the carrier;
a band being attached to the carrier and being arranged to hold the carrier against the limb of a user; and
an eye provided at a first end of the strap through which a free end of the band is threadable, so as to allow tensioning of the strap around the limb of the user,
wherein the band includes a first surface, the first surface and the inner surface both facing a first direction in an un-threaded state of the strap,
wherein the band includes a pattern provided on the first surface such that an increasing amount of the pattern becomes visible to the user when the strap is tensioned in a threaded state of the strap, the pattern indicating a length of the band being threaded through the eye to thereby indicate a single value of a plurality of predetermined degrees of tension being applied to the limb, and
wherein the band is stretchable so as to allow stretching of the band along a direction of extension of the band to achieve a desired degree of tension chosen from the plurality of predetermined degrees of tension indicated by the pattern.

13. The strap according to claim 12, wherein the pattern comprises one or more of lines, numbers and colours, the pattern having a shifting appearance along a length of the pattern.

14. The strap according to claim 12, wherein the strap comprises a first and a second fastening means provided on a second surface of the band, the second surface being opposite to the first surface, wherein the first fastening means is provided in a region of the free end of the band, and wherein the first fastening means is arranged to mate with the second fastening means when the band is folded in a threaded state of the strap to thereby fasten the band.

15. The strap according to claim 12, wherein the one or more magnets are supple.

16. The strap according to claim 12, wherein the strap comprises at least three elongated magnets being provided in the carrier such that a direction of extension of the elongated magnets coincides with a direction of extension of the strap.

17. The strap according to claim 16, wherein the at least three elongated magnets are provided in the carrier with a mutually alternating polarity.

18. The strap according to claim 12, wherein the eye is provided at a first end of the band, the first end being opposite to the free end, or at one end of the carrier.

19. The strap according to claim 12, wherein when the band is threaded through the eye, the desired degree of tension is a predetermined tension interval determined based on the pattern indicated between the eye at a first position on the pattern and the eye at a second position on the pattern.

20. The strap according to claim 19, wherein the band is not subject to tension in the first position.

\* \* \* \* \*